(12) United States Patent
Slaugh et al.

(10) Patent No.: US 6,545,192 B2
(45) Date of Patent: *Apr. 8, 2003

(54) PROCESS FOR SEPARATING OLEFINS FROM SATURATED HYDROCARBONS

(75) Inventors: Lynn Henry Slaugh, Houston, TX (US); Laurent Alain Fenouil, Houston, TX (US); Howard Lam-Ho Fong, Sugar Land, TX (US)

(73) Assignee: Shell Oil Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/309,417

(22) Filed: May 11, 1999

(65) Prior Publication Data

US 2002/0016523 A1 Feb. 7, 2002

(51) Int. Cl.[7] ............... C07C 7/148; C07C 7/152
(52) U.S. Cl. ............... 585/867; 585/865; 585/833; 585/807
(58) Field of Search ............... 585/867, 865, 585/833, 804, 26, 25

(56) References Cited

U.S. PATENT DOCUMENTS

| 3,674,885 | A | * | 7/1972 | Griesinger et al. ..... 260/671 B |
| 4,579,986 | A | | 4/1986 | Sie |
| 4,915,794 | A | | 4/1990 | Slaugh et al. .............. 203/29 |
| 4,946,560 | A | | 8/1990 | Slaugh et al. .............. 203/38 |
| 5,012,034 | A | | 4/1991 | Weingaertner et al. ..... 585/806 |
| 5,691,281 | A | | 11/1997 | Ashjian et al. |
| 5,811,623 | A | * | 9/1998 | Ryu et al. ............... 585/671 |
| 6,018,089 | A | | 1/2000 | Slaugh et al. |
| 6,211,423 | B1 | * | 4/2001 | Slaugh et al. ............. 585/867 |
| 6,271,434 | B1 | * | 8/2001 | Slaugh et al. ............. 585/867 |

FOREIGN PATENT DOCUMENTS

WO    WO 98/57911    12/1998

OTHER PUBLICATIONS

Hackh's Chemical Dictionary ; pp. 449, 50, and 85, 1969.*
Chemical Engineers' Handbook; Robert Perry; pp. 17–8 to 17–10, 1969.*
U.S. application Ser. No. 08/987,553, Slaugh et al., filed Dec. 9, 1997.
U.S. application Ser. No. 08/876,822, Slaugh et al., filed Jun. 16, 1997.
U.S. application Ser. No. 08/987,555, Suyherburgh et al., filed Dec. 9, 1997.
U.S. application Ser. No. 09/310,054, Slaugh et al., filed Jun. 11, 1999.

* cited by examiner

Primary Examiner—Thuan D. Dang

(57) ABSTRACT

A process for separating and isolating olefins from saturated hydrocarbons, preferably in a Fischer Tropsch stream, by adducting the olefins with a linear polyaromatic compound and separating the adducts from the remainder, which comprises saturated hydrocarbons.

53 Claims, No Drawings

PROCESS FOR SEPARATING OLEFINS FROM SATURATED HYDROCARBONS

FIELD OF THE INVENTION

This invention relates to a process for separating olefins from saturated hydrocarbons, and more particularly, to a process for separating olefins from saturated hydrocarbons in a Fisher-Tropsch (FT) stream.

BACKGROUND OF THE INVENTION

Many industrial processes produce olefin/saturated hydrocarbon streams that are mixtures of olefins, saturated hydrocarbons, and oxygenates. Olefins are frequently used in the manufacture of polymers such as polyethylene, as drilling mud additives, or as intermediates for the production of oil additives and detergents. Some industrial processes manufacture olefins streams by oligomerizing ethylene over an alpha olefin catalyst to produce mixtures of alpha and internal olefins having a broad range of carbon numbers. However, these streams rely on the use of ethylene as a feedstock material, which add a significant cost to the manufacture of the olefin. On the other hand, the FT process starts with an inexpensive feedstock, syngas, generally derived from natural gas, coal, coke, and other carbonaceous compounds to make oligomers comprised of olefins, aromatics, saturates, and oxygenates.

The FT process, however, is not very selective to the production of olefins. While reaction conditions and catalysts can be tuned to manufacture a stream rich in the desired species within the FT product stream, a large percentage of the FT stream contains other types of compounds which must be separated from the olefins, which olefins are purified, and then sold into different markets. For example, a typical commercial FT stream will contain a mixture of saturated hydrocarbons, olefins, and oxygenates such as organic carboxylic acids, alcohols, ethers, esters, ketones, and aldehydes. All these compounds must be separated from the crude FT stream before a particular composition may be offered commercially. To further complicate the separation operation, the FT stream contains compounds having a wide spectrum of carbon numbers, as well as a wide variety of olefins, ranging from $C_2$–$C_{200}$ species, internal linear olefins, alpha linear olefins, internal branched olefins, alpha branched olefins, and cyclic olefins, many of which have similar molecular weights. Separating and isolating these species is no easy task. Conventional distillation methods are frequently inadequate to separate species having closely related boiling points.

Various processes have been proposed to efficiently separate the different species in an FT stream with sufficient purity that a particular composition is acceptable in the intended application. These processes for separating out different species in an FT stream include the use of molecular sieves, which are restricted to a feed have an average carbon number range which is more limited than a composition containing a broad spectrum of average carbon numbers ranging from $C_5$–$C_{20}$, to the use of exchange resins, to the use of super-fractionaters often operated at high pressure, and the use of oligomerization catalysts or etherification techniques to alter the boiling points of the species in the FT stream. Many reactive methods for separating species in an FT stream do not, however, selectively react with olefins while simultaneously reject paraffins.

It would be desirable to conduct a separation operation on an FT stream in which the activity and life of the separating agent is not diminished by the presence of impurities in the stream, such as oxygenates; which remains active under a wide band of average carbon numbers ranging from $C_5$–$C_{20}$, and which distinguishes between olefins and paraffins in an FT stream.

U.S. Pat. No. 4,946,560 described a process for the separation of internal olefins from alpha olefins by contacting a feedstock with an adducting compound such as anthracene to form an olefin adduct, separating the adduct from the feedstock, dissociating the olefin adduct through heat to produce anthracene and an olefin composition enriched in alpha olefin, and separating out the anthracene from the alpha olefin. This reference does not suggest the desirability or the capability of anthracene to conduct a separation operation between saturated hydrocarbons and olefins.

SUMMARY OF THE INVENTION

This invention relates to a process for separating and optionally isolating olefins from saturated hydrocarbons, and in particular, to a process for separating and optionally isolating olefins from saturated hydrocarbons in an FT stream. There is provided a process for separating olefins from saturated hydrocarbons in a feedstock, comprising:

a) contacting a feedstock comprising olefins and saturated hydrocarbons with a linear polyaromatic compound under conditions effective to form a reaction mixture comprising linear polyaromatic compound-olefin adducts and saturated hydrocarbons;

b) separating the linear polyaromatic compound-olefin adducts from the saturated hydrocarbons in the reaction mixture to form a saturated hydrocarbon stream and an adducted olefin stream;

c) dissociating the linear polyaromatic compound-olefin adducts in the adducted olefin stream to form linear polyaromatic compounds and an olefin composition; and optionally d) separating the linear polyaromatic compound formed in step c) from the olefin composition;

whereby the olefin composition is enriched in the concentration of olefins over the concentration of olefins in the feedstock.

DETAILED DESCRIPTION OF THE INVENTION

As used throughout this specification and in the claims, the term "comprising" means "at least," such that other unmentioned elements, ingredients, or species are not excluded from the scope of invention.

The feed stream to be treated comprises at least olefins and saturated hydrocarbons. The class of saturated hydrocarbons as used herein includes at least a paraffin. The class of saturated hydrocarbons may also include other molecules such as cycloparaffins.

An olefin means any compound containing at least one carbon—carbon double bond. The olefins may be linear, branched, conjugated, contain multiple double bonds anywhere along the chain, substituted, unsubstituted, contain aryl or alicyclic groups, or contain heteroatoms.

The olefins may contain aryl moieties along with an aliphatic or cycloaliphatic moiety within the same compound, or may consist solely of an aliphatic, cycloaliphatic, or cycloaliphatic with aliphatic moieties on the compound. Preferably, the olefin is an aliphatic compound.

The olefin may be branched or linear. Examples of branching include alkyl, aryl, or alicyclic branches. The number of unsaturation points along the chain is also not limited. The olefin may be a mono-, di-, tri-, etc. unsaturated olefin, optionally conjugated. The olefin may also contain acetylenic unsaturation.

An alpha olefin is an olefin whose double bond is located on both of α and β carbon atoms. An a carbon atom is any terminal carbon atom, regardless of how long the chain is relative to other chain lengths in a molecule. The alpha olefin may be linear or branched. Branches or functional groups may be located on double bond carbon atoms, on carbon atoms adjacent to the double bond carbon atoms, or anywhere else along the carbon backbone. The alpha olefin may also be a poly-ene, wherein two or more points of unsaturation may be located anywhere along the molecule, so long as at least on double bond is in the alpha position.

An internal olefin(s) is an olefin whose double bond is located anywhere along the carbon chain except at any terminal carbon atom. The internal olefin may be linear or branched. The location of a branch or substitution on the internal olefin is not limited. Branches or functional groups may be located on the double bond carbon atoms, on carbon atoms adjacent to the double bond carbon atoms, or anywhere else along the carbon backbone.

The olefin may also be substituted with chemically reactive functional groups. Examples of chemically reactive functional groups are carboxyl, aldehyde, keto, thio, ether, hydroxyl, and amine. The number of functional groups on a molecule is not limited. The functional groups may be located anywhere along the carbon backbone.

The feedstock is generally produced by commercial processes such as the oligomerization of ethylene, optionally followed by isomerization and disproportionation. Alternatively, the feedstock may be produced by the Fisher-Tropsch process, which typically contains a high proportion of paraffins. A Fisher-Tropsch process catalytically hydrogenates CO to produce compositions containing aliphatic molecular chains. Other processes for making feedstocks which may contain mixtures of olefins and paraffins include the dehydrogenation of paraffin, such as those made by the Pacol™ processes of UOP, and the cracking of waxes. The most preferred feedstock is that obtained from a Fisher-Tropsch (FT) synthesis.

FT catalysts and reaction conditions can be selected to provide a particular mix of species in the reaction product stream. For example, the particular catalyst and reaction conditions may be tuned to enhance the amount of olefins and decrease the amount of paraffins and oxygenates in the stream. Alternatively, the catalyst and reaction conditions may be tuned to enhance the amount of paraffins and decrease the amount of olefins and oxygenates in the stream.

Generally, the reaction conditions will vary depending on the type of equipment employed. The FT reaction temperatures vary between 100° C. to 500° C., an inlet gas pressure to the reactor from atmospheric to 1500 psig, and an $H_2/CO$ ratio from 0.5:1 to 5:1, preferably from 1.8:1 to 2.2:1, and gas hourly space velocity ranging from 1 to 10,000 v/v/hour. A variety of reactor vessel configurations can be used, including a fluidized(entrained) bed, a fixed bed, and a slurried bed. The temperature in these beds can be adjusted by those of ordinary skill to optimize the formation of FT products, including hydrocarbons, and particularly, olefins and types of olefins. To illustrate without limitation, in fluidized (entrained) bed(s), the temperature of reaction is generally high—e.g. ranging from 280° to 350° C., preferably 310° to 340° C. If a fixed bed reactor(s) is used, the reaction temperature is generally ranges within 200° C. to 250° C., preferably between 210° and 240° C., and when a slurry bed reactor(s) is used, the temperature is generally within the range of 190° C. to 270° C.

The catalyst used in the FT process is any known in the art, but preferably from among Mo, W, and Group VIII compounds, including iron, cobalt, ruthenium, rhodium, platinum, palladium, iridium, osmium, combinations of the foregoing, combinations with other metals, and each being in the free metal form or as alloys, or as an oxide or carbide or other compound, or as a salt. Iron based and cobalt based catalysts have found common commercial use, and ruthenium has gained importance as a metal for the catalyst which favors the formation of high melting waxy species under high pressure conditions. Those of skill in the art recognize which catalysts and combinations will favor the manufacture of desired species in the FT reaction composition. For example, fused iron containing a promoter such as potassium or oxides on a silica, alumina, or silica-alumina support are known as FT synthetic catalysts. Another example is the use of Co metal. Cobalt has the advantage of producing less methane during synthesis over the older nickel based catalysts, and produces a wide spectrum of species. With the proper selection of supports, promoters, and other metal combinations, the cobalt catalyst can be tuned to manufacture a composition rich in the desired species. Other catalysts, such as iron-cobalt alloy catalysts, are known for their selectivity toward olefins under certain process conditions.

The catalysts may be fused or precipitated, or sintered, cemented, impregnated, kneading or melting onto a suitable support.

The catalysts may also contain promoters to promote the catalyst's activity, stability, or selectivity. Suitable promoters include alkali or alkaline earth metals, in free or combined form as an oxide, hydroxide, salt, or combinations thereof.

An FT stream generally contains virtually no sulfur or nitrogen compounds, which may be deleterious to other catalysts which derivatize the olefins or catalyze the reaction of olefins in other oligomerization or polymerization processes. Regardless of the method used, however, the FT process is not very selective to a particular species, and yields a wide variety of species within a composition.

Examples of some of the species found in any FT stream include paraffins having a broad spectrum of molecular weights, alcohols, acids, ketones, and aldehydes, and small amounts of aromatics. The linear polyaromatic compound used in the process of the invention, however, is particularly well adapted for the separation of olefins from saturated hydrocarbons in an FT stream in the presence of oxygenates since oxygenates do not significantly impair the performance of the linear polyaromatic compound.

While reference is made to a FT stream, it is to be understood that any stream made by any process containing olefins and saturated hydrocarbons are suitable feedstocks for the process of the invention. Most crude FT streams contain from 5% to 99% olefins, the remainder being saturated hydrocarbons comprising paraffins and cycloparaffins, and optionally other compounds such as aromatics optionally containing saturated or unsaturated alkyl branches, and oxygenates, based on the weight of all ingredients in the feedstock stream to the process of the invention. The preferred amount of olefin present in the FT stream ranges from 15 wt. % to 70 wt. %. The amount of linear alpha olefin in the FT stream is not limited, but preferably ranges from 15 wt. % to 60 wt. %. The amount of other olefins, including branched olefins and internal olefins, both linear and branched, is also not limited, but preferably ranges from 1 wt. % to 55 wt. %, more typically from 5 wt. % to 45 wt. %. The amount of paraffin in most FT streams range from 5 wt. % to 99 wt. %. In some FT streams, the FT catalyst is tuned to enhance the olefin concentration and decrease the paraffin concentration. In these streams, the amount of paraffin generally ranges from 5 to 65 wt. % of the stream. In other FT streams where the FT catalyst is tuned to enhance the amount of paraffin, the amount of paraffin in the stream ranges from 65 wt. % to 99 wt. %. The amounts of other compounds in a FT stream, such as oxygenates and aromatics, make up most of the remainder of the FT stream, and are generally present in amounts ranging from 5 wt. % to 30 wt. %. Minor amounts of other by-products and impurities, less than 5 wt. %, may be present in most FT streams. An FT stream which consists essentially of paraffins, olefins, aromatics and oxygenates can include such minor amounts of other by-products and impurities.

The feedstock may be a processed FT stream which has been fractionated and/or purified by a conventional distillation, extraction, or other separation operation to remove some of the paraffins, high and low molecular weight species, and oxygenates from the crude stream. When the separation operation is conducted by distilling the reaction mixture containing the adduct, it is preferred that the feedstock used in the process of the invention contain an average carbon number ranging from $C_5$–$C_{20}$ and wherein the predominant olefin species in the feedstock is within the range of $C_5$–$C_{20}$, inclusive. The polyaromatic adducting compound efficiently separates the saturated hydrocarbons from the olefins when the average carbon number of the feedstock and the predominant olefinic species is within this range, inclusive. When the average carbon number of the feedstock exceeds $C_{20}$, the polyaromatic compound-olefin adduct boils at a lower temperature than many of the species in the $C_{20}+$ feedstock composition, thereby leaving these high boiling species in the reaction mixture bottoms containing the adduct. Accordingly, the particular polyaromatic compound and the particular feedstock composition should be so selected that the polyaromatic compound-olefin adduct composition in the reaction mixture boils at a higher temperature than the amount of unreacted paraffin species in the feedstock one desires to separate. Therefore, in this preferred embodiment, the feedstock stream is one which contains an average carbon number ranging from $C_5$–$C_{20}$, and more preferably ranging from $C_6$–$C_{16}$, and wherein the predominant olefin species is within these ranges, inclusive. These types of FT streams are generally processed by one of the techniques identified above to substantially remove cuts containing ingredients below or exceeding the range of $C_5$–$C_{20}$.

In the event that one desires to employ a feedstock outside of the range of $C_5$–$C_{20}$, other separation techniques can be used to separate the adduct from the unreacted reaction mixture, including the selection of higher boiling polyaromatic compounds and/or other separation techniques such as liquid/liquid extraction or crystallization. These techniques, of course, can also be used with feedstocks within the range of $C_5$–$C_{20}$, inclusive.

The linear polyaromatic compound is utilized in the instant process to form the adduct with the olefins in the feed stream. As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to at all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain so long as at least three fused rings are present in a linear arrangement; as well as those containing a heteroatom which do not interfere in the separation of olefins from saturated hydrocarbons.

The linear polyaromatic compound has a preferential selectivity toward adducting with linear alpha olefin compounds, and secondly with other olefins, and last with paraffins, with which the compound is virtually unreactive under any operating condition outside of cracking conditions. The linear polyaromatic compound of choice is one which has a selectivity for linear alpha olefin compounds over other olefins greater than 1:1 by mole, preferably 2:1 or more, more preferably 4:1.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and not so large as to block the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

The process of the instant invention is basically at least a three step process wherein (a) a linear polyaromatic compound is reacted with a feedstock comprising saturated hydrocarbons and olefins to form an adduct of an olefin-linear polyaromatic compound, (b) the adduct is separated from the reaction mixture, typically by flashing or distilling the unreacted components comprising saturated hydrocarbons at the overhead and recovering the adduct as part of a bottoms stream, and (c) the adduct is dissociated to release the alpha olefin and regenerate the linear polyaromatic compound. The Diels-Alder adduct forming reaction is carried out in a conventional fashion and reaction zone. An example of a suitable reaction zone is a continuously stirred tank reactor, configured as a single unit, in parallel, or in series, wherein olefin and linear polyaromatic compound are added continuously to a stirred tank to form a liquid reaction mixture under heat, and the reaction mixture is continuously withdrawn from the stirred tank. Alternatively, the reaction may be carried out in a bubble column, or in a batch reactor, or utilize a plug flow reaction scheme.

The adducting reaction is typically carried one or more temperatures ranging from about 150° to about 290° C., preferably from about 200° to about 280° C., and most preferably from about 240° to about 265° C. Pressures are not critical and typically run from about atmospheric to about 100 atmospheres. The reaction can be carried out in the gas phase under vacuum or liquid phase or mixed gas-liquid phase, depending on the volatility of the feedstock, but generally in the liquid phase.

Stoichiometric ratios or an excess of either olefin or linear polyaromatic compound can be used to form the adducts. The molar ratio of olefin to linear polyaromatic compound is preferably from 0.25:1 up to 10:1. The residence time is for a time sufficient to adduct the desired amount of linear polyaromatic compound with the olefin. Typical residence times range from 30 minutes to 4 hours in a batch reaction.

An inert solvent can be utilized to dissolve the feedstock olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, isopentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

In one embodiment of the invention, however, the feedstock adduction, and particularly, the linear polyaromatic compound-olefin adduct formation is carried out in the absence of a solvent to improve the rate or reaction and avoid additional equipment and process steps for separating the solvent.

After the linear polyaromatic compound-olefin adduct has been formed, the reaction mixture flows to a separation vessel effective for separating the saturated hydrocarbons from the linear polyaromatic compound-olefin adduct to form a saturated hydrocarbon stream and an olefin adducted stream. Due to the large molecular weight and structural difference between the linear polyaromatic compound-olefin adduct and the saturated hydrocarbons in the reaction mixture, conventional separation techniques are quite suitable for removing the unreacted saturated hydrocarbons. For example, the non-adducted compounds may be removed at the overhead or in fractions by vacuum or flash distillation of the reaction mixture to leave the linear polyaromatic compound-olefin adduct and unreacted linear polyaromatic compound as a liquid bottoms. The non-adducted compounds which are removed include the saturated hydrocarbons, the aromatics, and the oxygenates such as the alcohols, ketones, acids, along with internal and branched olefins which did not form an adduct with the linear polyaromatic compound.

Alternatively, the linear polyaromatic compound-olefin adduct is separated by cooling the reaction mixture until the adduct crystallizes out, followed by filtration or centrifugation to remove the unreacted olefin.

In most cases, any unreacted linear polyaromatic compound will separate out with the linear polyaromatic compound-olefin adduct in the adducted olefin stream. Other ingredients, such as small amounts of higher molecular weight unreacted olefins, internal olefins, and branched olefins, may remain in the adducted olefin stream.

The next step of the instant process is to dissociate the linear polyaromatic compound-olefin adduct. The dissociation process can be accomplished by feeding the adducted olefins stream to a dissociation vessel where the adducted olefins stream is heated or pyrolyzed at a temperature effective to dissociate the adduct, typically from about 250° to about 500° C., preferably from about 300° to about 350° C. This pyrolysis frees the olefins from the linear polyaromatic compound. The linear polyaromatic compound is then separated from the resulting mixture by any conventional means, which may occur simultaneously with the pyrolysis operation, such as by vacuum or flash distilling off the olefins along with any impurities at the pyrolysis temperatures, and removing the linear polyaromatic compound as a bottoms from the adduct dissociation zone. Other separation techniques include filtration and centrifugation.

The linear polyaromatic compound may be recycled back to the adduct reaction zone. The separated olefin composition is now enriched in olefin concentration over that of the feedstock to the adduct reaction zone, and the concentration of saturated hydrocarbons in the olefin composition is reduced over that of the feedstock. Likewise, when the saturated hydrocarbons are separated from the linear polyaromatic compound-olefin adduct in the separation vessel as a saturated hydrocarbon stream, the saturated hydrocarbon stream is enriched in its concentration of saturated hydrocarbon over the concentration of saturated hydrocarbon in the feedstock to the adduct reaction zone, and the concentration of olefins in the saturated hydrocarbon stream is reduced over the concentration of olefins in the feedstock entering the adduct reaction zone. Each of the olefin composition and the saturated hydrocarbon stream may be recovered and isolated for use into other applications or as intermediates in other reactive processes.

For purposes of measuring the percentage reduction of a species in a stream, the concentration of the species or series of species in question contained in the product stream is subtracted from the concentration of the species or series of species in question contained in the feedstock, the difference then divided by the concentration of the same species in the feedstock multiplied by 100. For purposes of measuring the % enrichment of a species in a stream, the concentration of the species or series of species in the feedstock stream is subtracted from the concentration of species or series of species in question contained in the product stream, the difference then divided by the concentration of those same species present in the feedstock stream and multiplied by 100. For purposes of adding together a series of species, the sum total of the series in the feedstock stream is added, and then the sum total of the species in the product stream are added if the concentration of the particular species is enriched over that particular species in the feedstock stream, and subtracted if the concentration of the particular species is reduced from the concentration in the feedstock stream. The total in the product stream is then compared to the total in the feedstock stream to determine whether the total of the series in the product stream was enriched or reduced over the sum total in the feedstock stream. The appropriate calculation mentioned above is then applied depending on whether the series in the product stream were reduced or enriched.

The process of the invention will enrich the total concentration of olefins, enrich the concentration of linear alpha olefin, and reduce the concentration of saturated hydrocarbons, each in the olefin composition over the concentration of all olefins, linear alpha olefin and saturated hydrocarbons contained in the feedstock stream. The process of the invention will also enrich the concentration of saturated hydrocarbons present in the saturated hydrocarbon stream over the concentration of saturated hydrocarbon in the feedstock stream. The concentration of internal olefins and branched olefins in each of the saturated hydrocarbon streams and olefin composition may be enriched or reduced in each stream over the concentration of these ingredients present in the feedstock stream, for the reasons explained below.

In one embodiment, the concentration of all olefins in the saturated hydrocarbon stream are reduced through the process of the invention in only one pass by at least 15%, preferably at least 30%, more preferably at least 40%, over the concentration of all the olefins in the feedstock.

Since the linear polyaromatic compound is more selective towards adducting with linear alpha olefins relative to other olefins, the concentration of linear alpha olefins in the saturated hydrocarbon stream in another embodiment are reduced in one pass by at least 30%, more preferably by at least 40%, most preferably by at least 50%, over the concentration of linear alpha olefins present in the feedstock stream.

The amount of excess linear polyaromatic compound present in the adducting reaction zone, the residence time, and temperature, will affect the amount of internal or branched olefins adducting with the linear polyaromatic compound, and therefore, the amount of internal or branched olefins left unreacted and passing into the saturated hydrocarbon stream. While the linear polyaromatic compound preferentially adducts with a linear alpha olefin, the presence of a large excess of the polyaromatic compound relative to the amount of linear alpha olefins present in the feedstock coupled with long residence times, will leave un-adducted linear polyaromatic compounds free to adduct with the internal and branched olefins, thereby enhancing the reduction of these olefins in the saturated hydrocarbon stream over the concentration of these olefins in the feedstock stream. In another embodiment, the concentration of internal olefins present in the saturated hydrocarbon stream is reduced by from 1 to 50% over the concentration of linear internal olefins present in the feedstock.

With respect to the concentration of branched olefins, their concentration in the saturated hydrocarbon stream generally ranges to a slight reduction to an enrichment relative to the concentration of the branched olefins present in the feedstock. The concentration of branched olefins may be reduced by only 1 to 30%, or enriched by 1 to 30%, or remain unchanged, over the concentration of these branched olefins present in the feedstock.

The concentration of saturated hydrocarbon in the saturated hydrocarbon stream is enriched over the concentration of saturated hydrocarbon in the feedstock stream. In an embodiment of the invention, the concentration is enriched by at least 5%, preferably by at least 20%, and can be enriched by 100–400%, especially when the concentration of saturated hydrocarbon in the feedstock is low. Generally, the degree of enrichment of saturated hydrocarbon in the saturated hydrocarbon stream varies inversely with the concentration of the saturated hydrocarbons in the particular feedstock employed.

In another embodiment of the invention, the concentration of saturated hydrocarbons in the olefin composition is reduced through the process of the invention in only one pass by at least 80%, preferably by at least 90%, more preferably by at least 95% over the concentration of saturated hydrocarbon in the feedstock, and most preferably by 100%.

As above, the percentage reduction or enrichment of branched olefins and internal olefins in the olefin composition depends upon the amount of linear polyaromatic compound, temperature, and residence time of the feedstock in the adducting reaction zone. In one embodiment, the concentration of branched olefins in the olefin composition is reduced over the concentration of branched olefins in the feedstock. In another embodiment, the concentration of internal olefins in the olefin stream is enriched over the concentration of internal olefins present in the feedstock. The degree of enrichment of internal olefins in the olefin stream in another embodiment preferably ranges from 10% to 250%.

The concentration of linear alpha olefins in the olefin composition is enriched over the concentration of linear alpha olefins present in the feedstock stream. In an embodiment of the invention, the concentration of linear alpha olefins present in the olefin composition is enriched by at least 30%, more preferably by at least 40%, most preferably by at least 60%, over the concentration of linear alpha olefins present in the feedstock composition.

In another embodiment, the concentration of all olefins in the olefin composition is enriched over the concentration of all olefins in the feedstock stream. The degree of olefin enrichment varies inversely with the concentration of olefins present in the feedstock. In a preferred aspect of this embodiment, the concentration of all olefins in the olefin composition is enriched by at least 40%, preferably by at least 60%.

Fisher-Tropsch streams contain a variety of difficult to separate species, including saturated hydrocarbons, aromatics, oxygenates, internal olefins, branched olefins, and linear alpha olefins. An advantage of a Fisher-Tropsch stream is that it contains a mixture of both even and odd carbon, and the process of the invention produces a stream having even and odd carbon number olefin species at very low to zero amount of saturated hydrocarbons, with high concentrations of linear alpha olefins. The process of the invention can also provide a Fisher-Tropsch olefin composition having a mixture of internal olefins and/or branched olefins, and linear alpha olefins with low amounts of saturated hydrocarbons.

In one embodiment, the process of the invention provides a Fisher-Tropsch composition comprising odd and even numbered olefins, and the composition has an average carbon number ranging from $C_6$ to $C_{18}$, or optionally in the $C_6$ to $C_{12}$ range, comprising:

a) at least two linear alpha olefin species having different carbon chain lengths;

b) the two most predominant (on a mole basis) linear alpha olefin species of the at least two linear alpha olefin species are each within the range of $C_6$ to $C_{18}$, inclusive;

c) the two most predominant linear alpha olefin species are present in an amount of at least 20 wt %, preferably at least 30 wt. %, more preferably at least 40 wt. %, based on the weight of the olefins in the composition;

d) cumulatively, the total amount of linear alpha olefins present in the composition within said range, inclusive, is at least at least 40 wt. %, preferably at least 60 wt. %, more preferably at least 70 wt. %, and even 90 wt. % or more, based on the weight of the olefins in the composition;

e) one or more odd numbered olefins within the range present in an amount of at least 10 wt. %, preferably at least 20 wt. %, more preferably at least 30 wt. %, and even 40 wt. % or more, cumulative; and f) a cumulative amount of aromatics, saturated hydrocarbons, and oxygenates of 5 wt. % or less, preferably 2 wt. % or less, more preferably 1 wt. % or less, most preferably 0.5 wt. % or less, each based on the weight of the composition.

The treated Fisher-Tropsch composition may optionally contain branched olefins in an amount of at least 5 wt. % and even 10 wt. % or more, based on the weight of the olefins in the composition. Alternatively, or in addition to the branched olefins, the composition may contain internal olefins present in an amount ranging from 5 wt. % to 20 wt. %. Such feedstock streams may have a cost advantage in some processes, such as in those hydroformylation processes which are not very sensitive to the position of the double bonds in the feedstock for the manufacture of primary alcohols.

In another embodiment of the invention, the above mentioned composition has as one of the two most predominant olefin species an odd carbon number linear alpha olefin.

In another embodiment of the invention, there is provided a treated Fisher-Tropsch composition having an average carbon number ranging from $C_6$ to $C_{18}$ comprising at least two linear alpha olefin species having different carbon chain lengths within said range, inclusive, at least 50 wt. % of linear alpha olefins, where the composition has a most predominant olefin species represented by n carbon numbers, wherein the next most predominant olefin species has either n+1 or n−1 carbon numbers; and wherein said composition comprises 2 wt. % or less of saturated hydrocarbons.

The process of the invention advantageously provides an olefin stream which is highly concentrated in olefins, wherein the concentration of olefins in the olefin composition may be at least 90% and up to 100% olefin purity in the olefin composition.

The olefin composition stream of the invention is useful as a component in drilling fluids, to react with elemental sulfur to make sulfurized products as extreme pressure agents in metal working fluids, as a co-monomers for the polymerization of polyethylene, as an intermediate in making polyalpha olefins (PAO) used as a lubricant, as a chlorination feed to make polychlorinated hydrocarbons in PVC applications, to react with hydrogen sulfides to make primary and secondary mercaptans as pharmaceutical intermediates and as additives to modify the properties of rubber, as solvents, and as a precursor for the manufacture of plasticizer alcohols and detergent range alcohols and surfactants, which may be derivatized into detergent range sulfates or alkoxysulfates for laundry liquids and powders, dishwashing powders and liquids, bar soap, shampoo, liquid hand soap, and hard surface cleaners.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention. The present invention will now be illustrated by means of the following illustrative embodiments and examples which are provided for illustration and are not to be construed as limiting the invention.

EXAMPLE 1

To illustrate the concept of the invention, a Fisher-Tropsch stream comprised of the composition set forth in Table 1 was used as a feedstock. The FT composition was derived by passing syngas over an FT catalyst and subsequently distilling products in the boiling point range of hexyl to undecyl hydrocarbons. This composition was used as the feed. Hydrocarbons in the $C_7$–$C_{10}$ were the most abundant.

0.24 moles (42.2 g) of anthracene having a 95% purity and 150 g of the feedstock were placed in an autoclave. The total olefin content of the charged feed was about 0.5 moles (55.9 g). The autoclave was sealed and then purged with nitrogen. The autoclave was heated to 255° C. for four hours to form the Diels-Alder adduct between the olefin and the anthracene. The autoclave contents were stirred during heating.

Once the reaction was complete, the autoclave was cooled to 20° C. The product mixture was transferred to a glass flask and the unreacted olefin, saturated hydrocarbons, and unreacted oxygenates were removed by distillation. The material remaining in the flask (18.2 g) consisted of some entrained saturated hydrocarbons, unreacted anthracene, and the anthracene-olefin adduct. The flask and its contents were then heated to a temperature ranging from 310–350° C. to dissociate the adduct to anthracene and Product A described in Table 1 below. Product A was separated and isolated from the anthracene by distillation. The compositions of each Product stream were analyzed by gas chromatography.

As can be seen from the data in Table 1, Product A is greatly enriched in alpha olefin content and overall olefin content over the concentration of alpha olefin and overall olefin content in the feedstock stream. Product A is enriched in alpha olefin content by 205%, and in overall olefin content, Product A was enriched by 155% ([(86.5+8.9)−(28.3+9.0)]/(9.0+28.3)×100).

Further, the concentration of saturated hydrocarbon (exclusive of oxygenates) in Product A stream was greatly reduced; by 91%. The presence of saturated hydrocarbons in Product A is due to its incomplete removal upon distillation of the unreacted material from the adduct before the dissociation step. The concentration of internal olefin in Product A stream was only marginally reduced over the concentration of internal olefin present in the feedstock.

Product B represents the saturated hydrocarbon stream at the overhead on the distillation column taken from the reaction mixture. As can be seen from Table 1, Product B is enriched in saturated hydrocarbons over the concentration of saturated hydrocarbons in the feedstock stream, by 38%. The concentration of alpha olefin in the saturated hydrocarbon stream was reduced by 67% over the concentration of alpha olefin in the feedstock.

TABLE 1

SEPARATION OF SATURATED HYDROCARBONS FROM OLEFINS

| COMPOSITION | TOTAL WEIGHT (g) | SATURATED HYDROCARBONS (wt. %)[1] | INTERNAL OLEFINS (wt. %) | ALPHA OLEFINS (w %) | OXYGENATES (wt. %) |
|---|---|---|---|---|---|
| Feedstock | 150 | 56.7 | 9.0 | 28.3 | 6.0 |
| Product A | 18.2 | 4.6 | 8.9 | 86.5 | Trace |
| Product B | 62 | 78.2 | 7.2 | 9.3 | 5.3 |

[1]Exclusive of oxygenates

EXAMPLE 2

In this example, an F-T stream having the composition set forth in Table 2 was treated with anthracene. This F-T stream was derived by passing syngas over an FT catalyst and subsequently distilling and collecting the products in the boiling point range of pentyl to nonyl ($C_5$–$C_9$).

0.6 moles (112 g) of anthracene having a 95% purity and 96 g of the feedstock were placed in a 300 ml autoclave. The autoclave was sealed and then purged with nitrogen. The autoclave was heated to 255° C. for seven hours to form the Diels-Alder adduct between the olefin and the anthracene. The autoclave contents were stirred during heating.

Once the reaction was complete, the autoclave was cooled to 20° C. The product mixture was transferred to a glass flask and the unreacted olefin, saturated hydrocarbons, and unreacted oxygenates were removed from the reaction mixture by distillation. The material remaining in the flask was heated to a temperature ranging from 300–350° C. to dissociate the adduct to anthracene and Product A described in Table 2 below. Product A was separated and isolated from the anthracene by distillation. The compositions of each Product stream were analyzed by gas chromatography.

As can be seen from the data in Table 2, Product A is greatly enriched in alpha olefin content and overall olefin content over the concentration of alpha olefin and overall olefin content in the feedstock stream. Product A is enriched in alpha olefin content by 579%, and in overall olefin content, Product A was enriched by 348%. The olefin purity in Product A olefin stream was 100%. The concentration of internal olefin in Product A stream was increased over the concentration of internal olefin present in the feedstock by an amount of 163%.

TABLE 2

SEPARATION OF SATURATED HYDROCARBONS FROM OLEFINS

| COMPOSITION | TOTAL WEIGHT (g) | SATURATED HYDROCARBONS (wt. %)[1] | INTERNAL OLEFINS (wt. %) | ALPHA OLEFINS (w %) | OXYGENATES (wt. %) |
|---|---|---|---|---|---|
| Feedstock | 96 | 72 | 12.4[a] | 9.9 | 5.7 |
| Product A | 9.0 | 0 | 32.7 | 67.3 | 0 |

[a]66 wt. % of 2-olefins and 35 wt. % of other internal olefins
[1]Exclusive of oxygenates

What is claimed is:

1. A process for separating olefins from saturated hydrocarbons in a feedstock, comprising:
   a) contacting a feedstock comprising olefins and saturated hydrocarbons with a linear polyaromatic compound having at least three fused aromatic rings under conditions effective to form a reaction mixture comprising linear polyaromatic compound-olefin Diels Alder adducts and saturated hydrocarbons;
   b) separating the linear polyaromatic compound-olefin adducts from the saturated hydrocarbons in the reaction mixture to form a saturated hydrocarbon stream and an adducted olefin stream;
   c) dissociating the linear polyaromatic compound-olefin adducts to form linear polyaromatic compounds and an olefin composition,
   whereby the olefin composition is enriched in the concentration of olefins over the concentration of olefins in the feedstock.

2. A process for separating olefins from saturated hydrocarbons in a feedstock, comprising:
   a) contacting a feedstock comprising a stream derived from a Fisher-Tropsch process, said stream comprising olefins and saturated hydrocarbons with a linear polyaromatic compound having at least three fused aromatic rings under conditions effective to form a reaction mixture comprising linear polyaromatic compound-olefin adducts and saturated hydrocarbons;
   b) separating the linear polyaromatic compound-olefin Diels Alder adducts from the saturated hydrocarbons in the reaction mixture to form a saturated hydrocarbon stream and an adducted olefin stream;
   c) dissociating the linear polyaromatic compound-olefin adducts to form linear polyaromatic compounds and an olefin composition;
   whereby the olefin composition is enriched in the concentration of olefins over the concentration of olefins in the feedstock.

3. A process for separating olefins from saturated hydrocarbons in a feedstock, comprising:
   a) a feedstock having an average carbon number ranging from $C_5$–$C_{20}$ and having a predominant olefin species within said range, said feedstock comprising olefins and saturated hydrocarbons, and contacting said feedstock with a linear polyaromatic compound having at least three fused aromatic rings under conditions effective to form a reaction mixture comprising linear polyaromatic compound-olefin adducts and saturated hydrocarbons;
   b) separating the linear polyaromatic compound-olefin Diels Alder adducts from the saturated hydrocarbons in the reaction mixture to form a saturated hydrocarbon stream and an adducted olefin stream;
   c) dissociating the linear polyaromatic compound-olefin adducts to form linear polyaromatic compounds and an olefin composition; and
   d) separating the linear polyaromatic compounds formed in step c) from the olefin composition;
   whereby the olefin composition is enriched in the concentration of olefins over the concentration of olefins in the feedstock, and the saturated hydrocarbon stream is enriched in the concentration of saturated hydrocarbons over the concentration of saturated hydrocarbon in the feedstock.

4. A process for separating olefins from saturated hydrocarbons in a feedstock, comprising:
   a) a Fisher-Tropsch feedstock having an average carbon number ranging from $C_6$–$C_{16}$ and having a predominant olefin species within said range, said feedstock comprising linear alpha olefins, olefins other than linear alpha olefins, and saturated hydrocarbons, and contacting said feedstock with a linear polyaromatic compound comprising anthracene or benzanthracene under conditions effective to form a reaction mixture comprising linear polyaromatic compound-olefin Diels Alder adducts and saturated hydrocarbons;
   b) separating the linear polyaromatic compound-olefin adducts from the saturated hydrocarbons in the reaction mixture by distillation to form a saturated hydrocarbon stream and an adducted olefin stream;
   c) dissociating the linear polyaromatic compound-olefin adducts to form linear polyaromatic compounds and an olefin composition; and
   d) separating the linear polyaromatic compounds formed in step c) from the olefin composition;
   whereby the olefin composition is enriched in the concentration of olefins over the concentration of olefins in the feedstock, the saturated hydrocarbon stream is enriched in the concentration of saturated hydrocarbons over the concentration of saturated hydrocarbon in the feedstock, the concentration of linear alpha olefins in the olefin composition is enriched by at least 40% over the concentration of linear alpha olefins present in the feedstock stream, and the concentration of saturated hydrocarbons in the olefin composition is reduced by at least 90% over the concentration of saturated hydrocarbons present in the feedstock.

5. A process for separating olefins from saturated hydrocarbons in a feedstock, comprising:
  a) a Fisher-Tropsch feedstock having an average carbon number ranging from $C_6$–$C_{16}$ and comprising saturated hydrocarbons and olefins, said olefins having a predominant olefin species within said range, said olefins comprising linear alpha olefins and olefins other than linear alpha olefins, and contacting said feedstock with one or more linear polyaromatic compounds selected from the group consisting of anthracene, benzanthracene, and combinations thereof, under conditions effective to form a reaction mixture comprising said saturated compounds and Diels Alder adducts comprising said one or more linear polyaromatic compounds adducted with said olefins;
  b) separating said Diels Alder adducts from said saturated hydrocarbons by distillation to form a saturated hydrocarbon stream and a Diels Alder adduct stream;
  c) dissociating said Diels Alder adducts to form said one or more linear polyaromatic compounds and an olefin composition; and
  d) separating said linear polyaromatic compounds from said olefin composition; whereby said olefin composition is enriched in the concentration of said olefins over the concentration of said olefins in said feedstock, said saturated hydrocarbon stream is enriched in the concentration of said saturated hydrocarbons over the concentration of said saturated hydrocarbons in said feedstock, the concentration of said linear alpha olefins in said olefin composition is enriched by at least 40% over the concentration of said linear alpha olefins present in said feedstock, and the concentration of said saturated hydrocarbons in said olefin composition is reduced by at least 90% over the concentration of said saturated hydrocarbons in said feedstock.

6. A process for separating olefins from saturated hydrocarbons in a feedstock, comprising:
  a) contacting a feedstock comprising olefins and saturated hydrocarbons with one or more linear polyaromatic compounds having at least three fused aromatic rings under conditions effective to form a reaction mixture comprising said saturated hydrocarbons and Diels Alder adducts comprising said one or more linear polyaromatic compounds adducted with said olefins;
  b) separating said Diels Alder adducts from said saturated hydrocarbons in the reaction mixture to form a saturated hydrocarbon stream and a Diels Alder adduct stream;
  c) dissociating said Diels Alder adducts to form said linear polyaromatic compounds and an olefin composition; whereby said olefin composition is enriched in the concentration of said olefins over the concentration of said olefins in said feedstock.

7. The process of claim 6 wherein said feedstock is contacted with said linear polyaromatic compound at a temperature ranging from 150° to about 290° C.

8. The process of claim 7 wherein said feedstock is contacted with said linear polyaromatic compound at a temperature ranging from about 220° to about 265° C.

9. The process of claim 6 wherein the molar ratio of said olefins in said feedstock to said linear polyaromatic compounds ranges from greater than 0.25:1 to 10:1.

10. The process of claim 6 wherein said dissociating said Diels Alder adducts comprises heating said Diels Alder adducts to a temperature ranging from about 250° C. to 500° C.

11. The process of claim 10 wherein said heating said Diels Alder adducts comprises heating to a temperature ranging from about 300° C. to 350° C.

12. The process of claim 10 wherein the amount of paraffin ranges from 5 to 65 wt. % based on the weight of all ingredients in said feedstock.

13. The process of claim 6 wherein said linear polyaromatic compounds formed in (c) are separated from said olefin composition by vacuum or flash distillation.

14. The process of claim 10 wherein the amount of paraffin in said feedstock ranges from 65 wt. % to 99 wt. %.

15. The process of claim 6, wherein said separating in (b) is carried out by first cooling said reaction mixture followed by filtration or centrifugation.

16. The process of claim 6 wherein said feedstock comprises a stream derived from a Fisher-Tropsch process.

17. The process of claim 16 wherein said feedstock comprises from 15 wt. % to 70 wt. % olefin, based on the weight of all ingredients in said feedstock.

18. The process of claim 17 wherein said feedstock comprises from 15 wt. % to 60 wt. % linear alpha olefin, based on the weight of all ingredients in said feedstock.

19. The process of claim 18 wherein the amount of all olefins in said feedstock other than linear alpha olefins ranges from 1 wt. % to 55 wt. %, based on the weight of all ingredients in said feedstock.

20. The process of claim 17 wherein said feedstock comprises paraffins in an amount ranging from 5 wt. % to 99 wt. % based on the weight of all ingredients in said feedstock.

21. The process of claim 6 wherein the amount of all olefins other than linear alpha olefins in said feedstock ranges from 5 wt. % to 45 wt. %, based on the weight of all ingredients in said feedstock.

22. The process of claim 6 wherein said feedstock comprises oxygenates and aromatics collectively present in said feedstock in an amount ranging from 5 wt. % to 30 wt. %, based on the weight of all ingredients in said feedstock.

23. The process of claim 6 wherein said feedstock has an average carbon number ranging from $C_5$–$C_{20}$ and wherein the predominant olefin species in said feedstock is within the range of $C_5$–$C_{20}$, inclusive.

24. The process of claim 6 wherein the total concentration of said olefins and the concentration of linear alpha olefins is enriched in said olefin composition over the concentration of said olefins and said linear alpha olefins in said feedstock, and the concentration of saturated hydrocarbons is reduced in said olefin composition over the concentration of saturated hydrocarbons in said feedstock.

25. The process of claim 6 wherein said saturated hydrocarbon stream in enriched in its concentration of saturated hydrocarbons over the concentration of saturated hydrocarbons in said feedstock.

26. The process of claim 25 wherein said saturated hydrocarbon stream comprises olefins, and the concentration of all olefins in said saturated hydrocarbon stream are reduced in one pass by at least 15% over the concentration of all olefins present in said feedstock.

27. The process of claim 26 wherein the concentration of all olefins in said saturated hydrocarbon stream are reduced in one pass by at least 30%.

28. The process of claim 26 wherein the concentration of all olefins in said saturated hydrocarbon stream are reduced in one pass by at least 40%.

29. The process of claim 25 wherein said saturated hydrocarbon stream comprises linear alpha olefins, and wherein the concentration of linear alpha olefins in said saturated hydrocarbon stream are reduced in one pass by at least 30% over the concentration of linear alpha olefins present in said feedstock.

30. The process of claim 29 wherein the concentration of linear alpha olefins in said saturated hydrocarbon stream are reduced in one pass by at least 40% over the concentration of linear alpha olefins present in said feedstock.

31. The process of claim 30 wherein the concentration of linear alpha olefins in said saturated hydrocarbon stream are reduced in one pass by at least 50% over the concentration of linear alpha olefins present in said feedstock.

32. The process of claim 25 wherein the concentration of saturated hydrocarbons in said saturated hydrocarbon stream is enriched by at least 20% over the concentration of saturated hydrocarbons in said feedstock.

33. The process of claim 6 wherein the concentration of saturated hydrocarbons in said olefin composition is reduced in one pass by at least 80% over the concentration of saturated hydrocarbons in said feedstock.

34. The process of claim 33 wherein the concentration of saturated hydrocarbons in said olefin composition is reduced in one pass by at least 90% over the concentration of saturated hydrocarbons in said feedstock.

35. The process of claim 34 wherein the concentration of saturated hydrocarbons in said olefin composition is reduced in one pass by at least 95% over the concentration of saturated hydrocarbons in said feedstock.

36. The process of claim 6 wherein the concentration of saturated hydrocarbons in said olefin composition is reduced in one pass by 100% over the concentration of saturated hydrocarbons in said feedstock.

37. The process of claim 6 wherein said feedstock comprises branched olefins, and the concentration of branched olefins in said olefin composition is reduced over the concentration of branched olefins in said feedstock.

38. The process of claim 6 wherein the feedstock comprises internal olefins, and the concentration of internal olefin in said olefin composition is enriched by 10% to 250% over the concentration of internal olefin present in said feedstock.

39. The process of claim 6 wherein said feedstock comprises linear alpha olefins, and the concentration of linear alpha olefins in said olefin composition is enriched over the concentration of linear alpha olefins present in said feedstock.

40. The process of claim 39 wherein the concentration of linear alpha olefins present in said olefin composition is enriched by at least 30% over the concentration of linear alpha olefins present in said feedstock.

41. The process of claim 40 wherein the concentration of linear alpha olefins present in said olefin composition is enriched by at least 40% over the concentration of linear alpha olefins present in said feedstock.

42. The process of claim 41 wherein the concentration of said olefins in said olefin composition is enriched by at least 60% over the concentration of said olefins in said feedstock.

43. The process of claim 6 wherein said feedstock consists essentially of saturated hydrocarbons, oxygenates, aromatics, and olefins, and the concentration of olefins in said olefin composition ranges from about 90% to 100%.

44. The process of claim 6 wherein the average carbon number of said olefins ranges from 6 to 16, and the predominant olefin species in said feedstock is within said range, inclusive.

45. A process for separating olefins from saturated hydrocarbons in a feedstock, comprising:
a) a feedstock having an average carbon number ranging from $C_5$–$C_{20}$ and having a predominant olefin species within said range, said feedstock comprising olefins and saturated hydrocarbons, and contacting said feedstock with one or more linear polyaromatic compounds having at least three fused aromatic rings under conditions effective to form a reaction mixture comprising said saturated hydrocarbons and Diels Alder adducts comprising said one or more linear polyaromatic compounds adducted with said olefins;
b) separating said Diels Alder adducts from said saturated hydrocarbons in said reaction mixture to form a saturated hydrocarbon stream and an adducted olefin stream;
c) dissociating said Diels Alder adducts to form said one or more linear polyaromatic compounds and an olefin composition; and
d) separating said one or more Linear polyaromatic compounds from said olefin composition;
whereby said olefin composition is enriched in the concentration of said olefins over the concentration of said olefins in said feedstock, and said saturated hydrocarbon stream is enriched in the concentration of said saturated hydrocarbons over the concentration of said saturated hydrocarbons in said feedstock.

46. The process of claim 45 wherein said feedstock comprises a Fisher-Tropsch stream.

47. The process of claim 46 wherein said feedstock comprises from 15 wt. % to 60 wt. % linear alpha olefin, from 5 wt. % to 45 wt. % olefins other than linear alpha olefins, 5 wt. % to 99 wt. %. paraffins, and 15 wt. % to 30 wt. % oxygenates and aromatics.

48. The process of claim 47 wherein said one or more linear polyaromatic compounds are selected from the group consisting of anthracene, benzanthracene, and a combination thereof.

49. The process of claim 47 wherein said feedstock comprises linear alpha olefins, and the concentration of said linear alpha olefins in said olefin composition is enriched by at least 40% over the concentration of said linear alpha olefins in said feedstock, and the concentration of said saturated hydrocarbons in said olefin composition is reduced by at least 90% over the concentration of said saturated hydrocarbons in said feedstock.

50. A process for separating olefins from saturated hydrocarbons in a feedstock, comprising:
a) a feedstock comprising a Fisher-Tropsch stream and having an average carbon number ranging from $C_5$–$C_{20}$ and having a predominant olefin species within said range, said feedstock comprising olefins and saturated hydrocarbons, and contacting said feedstock with a linear polyaromatic compound having at least three fused aromatic rings under conditions effective to form a reaction mixture comprising linear polyaromatic compound-olefin Diels Alder adducts and saturated hydrocarbons;
b) separating the linear polyaromatic compound-olefin adducts from the saturated hydrocarbons in the reaction mixture to form a saturated hydrocarbon stream and an adducted olefin stream;
c) dissociating the linear polyaromatic compound-olefin adducts to form linear polyaromatic compounds and an olefin composition; and
d) separating the linear polyaromatic compounds formed in step c) from the olefin composition;

whereby the olefin composition is enriched in the concentration of olefins over the concentration of olefins in the feedstock, and the saturated hydrocarbon stream is enriched in the concentration of saturated hydrocarbons over the concentration of saturated hydrocarbon in the feedstock.

51. The process of claim 50, wherein the feedstock comprises from 15 wt. % to 60 wt. % linear alpha olefin, from 5 wt. % to 45 wt. % olefins other than linear alpha olefins, 5 wt. % to 99 wt. % paraffins, and 15 wt. % to 30 wt. % oxygenates and aromatics.

52. The process of claim 51, wherein the linear polyaromatic compound comprises anthracene or benzanthracene.

53. The process of claim 51, wherein the feedstock comprises linear alpha, and the concentration of linear alpha olefins in the olefin composition is enriched by at least 40% over the concentration of linear alpha olefins present in the feedstock stream, and the concentration of saturated hydrocarbons in the olefin composition is reduced by at least 90% over the concentration of saturated hydrocarbons present in the feedstock.

* * * * *